United States Patent [19]

Libby et al.

[11] Patent Number: Plant 5,345

[45] Date of Patent: Nov. 20, 1984

[54] REDWOOD TREE

[75] Inventors: William J. Libby, Orinda, Calif.; Kwabena Tufuor, Kumasi, Ghana

[73] Assignee: The Regents of the University of California, Berkeley, Calif.

[21] Appl. No.: 481,101

[22] Filed: Mar. 31, 1983

[51] Int. Cl.[3] ..... A01H 7/00

[52] U.S. Cl. ..... Plt./50

[58] Field of Search ..... Plt./50

*Primary Examiner*—Robert E. Bagwill

*Attorney, Agent, or Firm*—Townsend and Townsend

[57] ABSTRACT

A new variety of coast redwood useful for Christmas tree and ornamental purposes. The new variety exhibits dense columnar form with upturning lower branches. The growth rate is significantly slower than that of a normal redwood. The new variety does well in full sunlight or partial shade. The foliage color remains green throughout the year. The new variety can be reproduced on a commercial scale by rooting branch cuttings.

5 Drawing Figures

This invention was made with Government support under Grants 2550 and 5053 awarded by the National Science Foundation. The Government has certain rights in this invention.

The present invention relates to a new and distinct variety of coast redwood (*Sequoia sempervirens*). The variety name is Korbel KT.

The new variety was discovered as part of a research project investigating the maturation state of rooted cuttings taken from several parts of 300- to 500-year-old redwood trees growing near Korbel, Humboldt County, Calif. Numerous branches were cut from each of six felled trees. These branches were labeled to identify the tree and the part of the tree from which they were taken.

Cuttings, from the various labeled branches, were rooted in 1966. Subsets of the rooted cuttings were planted during the winter of 1966–1967 at the University of California Gill Tract in Albany, Calif.

In 1970 six rooted cuttings under cultivation at Gill Tract were discovered to be different from all others in the experiment. After checking the identity of the six plants, it was determined that they had been taken from a single upper crown branch with bilateral symmetry. Hundreds of other rooted cuttings from many other branches taken from the same tree were normal in all respects. These six cuttings, which apparently are from a sport, were the original plants of the new variety. Additional cuttings have been taken from the six original plants of the new variety and rooted in various places since 1973 to further test the growth, adaptability and characteritics of the new variety.

Figure 4:
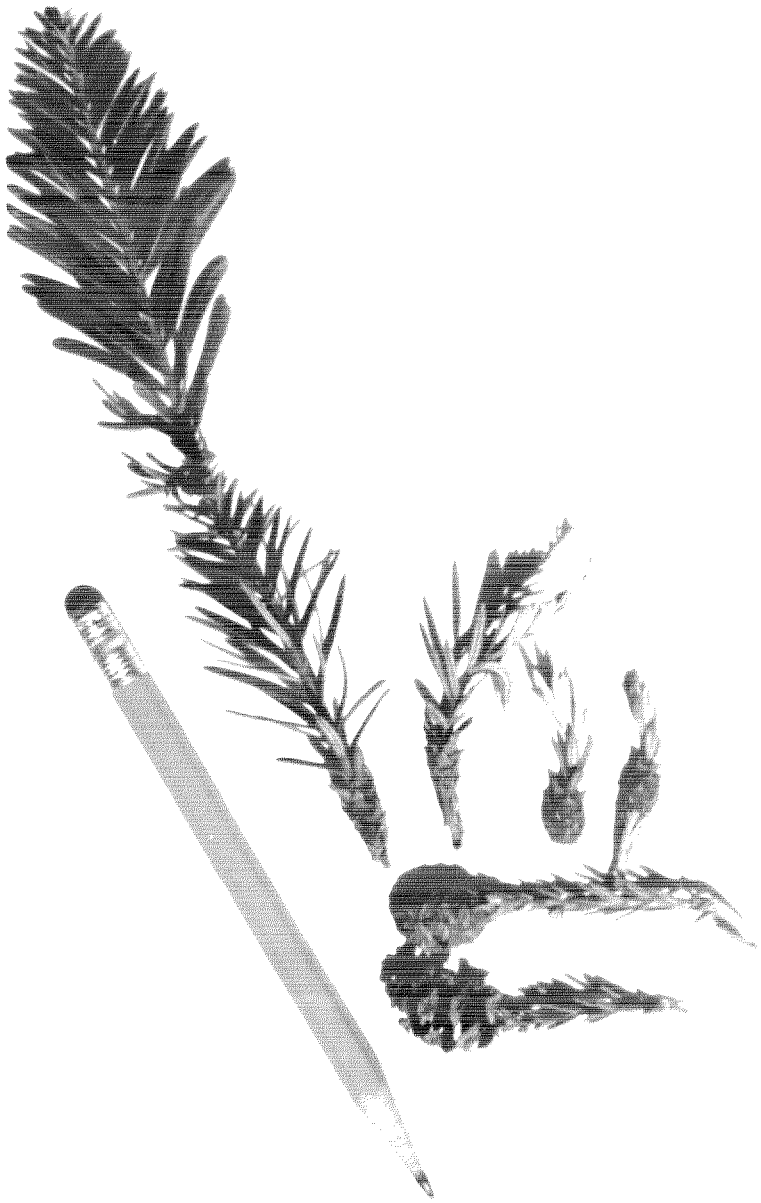

FIG. 4, in the upper portion of the photograph, illustrates four twigs from a tree of the new variety that began as female strobili (cones) and which then continued their development as branches; the two twigs at the bottom illustrate normal cone development from two normal redwoods with cones terminating branch development.

Figure 5:
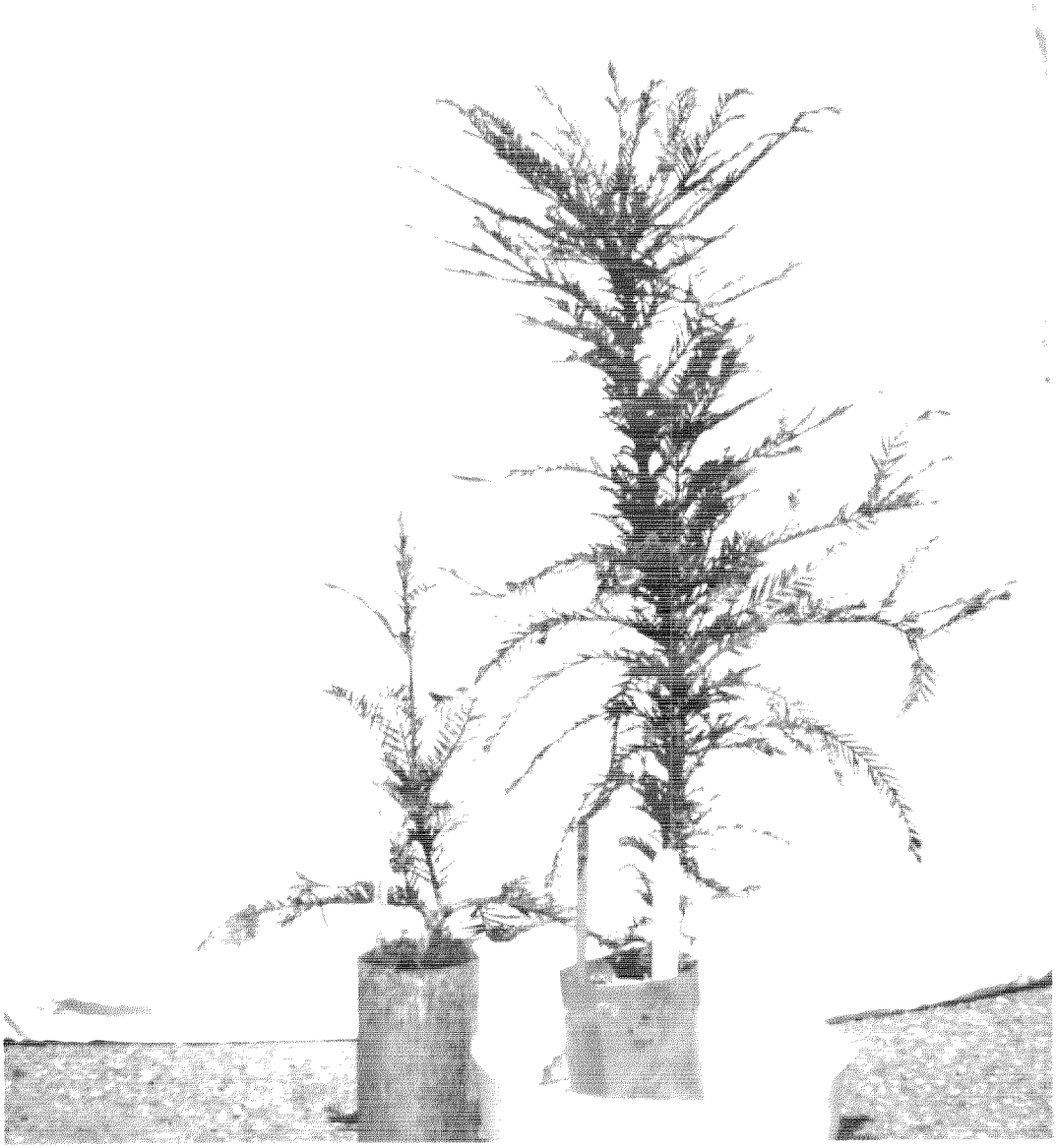

FIG. 5 illustrates the size and form of recently rooted (left) and yearling (right) plants of the new variety.

PLANT CHARACTERISTICS

The color references listed below refer to the Munsell Color System—Nickerson Color Fan.

The most distinguishing characteristics of the new variety are its relatively small size and its radial, rather than bilateral, symmetry when grown from cuttings. It is suited as an ornamental for bordering walkways, driveways and residential landscaping. It has a pleasing color and form, and will not rapidly grow to overtop the walk or house. The new variety does well in full sunlight or partial shade, but reverts to branch form in full shade. It grows well in large or small containers, and responds well to repeated pruning. The new variety appears to be missing one or more chromosomes. If harvested for use as a Christman tree or for other uses, the new variety will generally sprout from the stump producing several new shoots. The new shoots can be thinned to a single shoot after about a year.

HABIT

Figure 1:
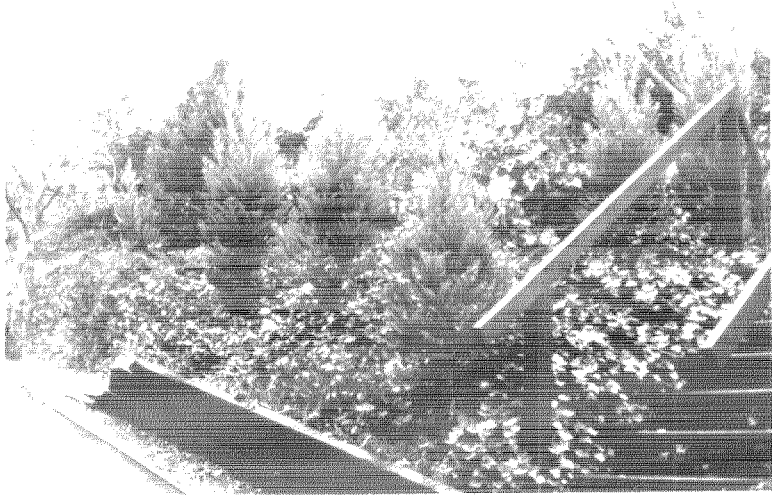
FIG. 1 illustrates the color and growth habit of the plant used as a drive and stair border.

Dense columnar growth frequently with upturning lower branches (FIG. 1).

GROWTH RATE

Figure 2:
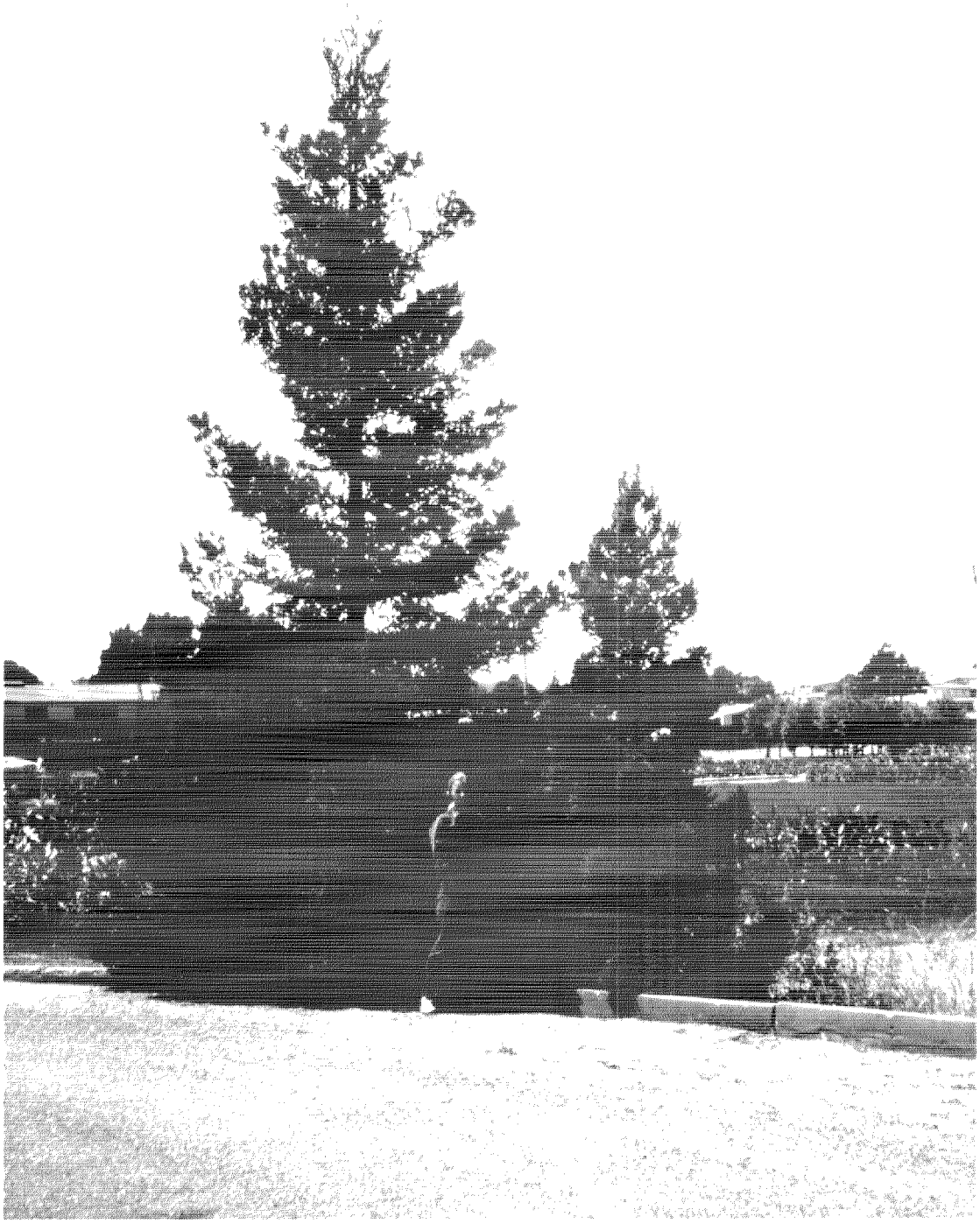
FIG. 2 illustrates relative growth rates of the new variety (right) and a normal juvenile redwood (left). The taller normal redwood was planted one year later than the new variety.

About ½ to ⅓ that of normal redwood, depending on site. This slower growth rate is illustrated in FIG. 2. The normal redwood (on the left) and new variety (on the right) in FIG. 2 are both about 10 years old. The site of the trees shown in FIG. 2 is a poor one. At a better site these trees would be larger and their difference in size would be smaller.

INSECTS AND DISEASES

None have been noted. Redwood in general is relatively free of epidemic pests and diseases. Several other redwoods in the 1966 experiment were damaged by stem-boring insects, but trees of the new variety have not been damaged.

COLD, DROUGHT, HEAT, WIND, SOIL

In tests thus far, no unusual requirements or tolerances have been noted. At present, it seems reasonable to expect survival and good performance where normal redwood is successfully grown. The new variety handles smog in Riverside, Orange and Los Angeles County test sites without obvious damage.

LEAVES AND FLOWERS

Figure 3:
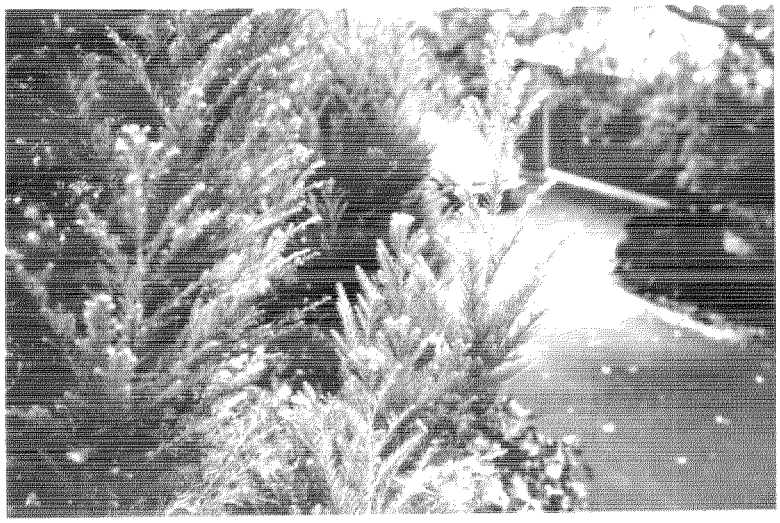
FIG. 3 is a close-up of a typical branch, illustrating short dense leaves, dark geen color, and light-colored winter twig ends.

Leaves are small-to-normal in size. The leaves are typically green (10.0GY ¾) to bluish-green (7.5G 4/2) as shown in FIG. 3. One unusual feature is that, unlike most juvenile redwoods, this color does not change to bronze in winter, but stays the same even following a substantial chill. The compact winter meristem typically is a light buff (7.5Y 8/6) of yellowish (5.0Y 8/4) color, providing a contrast to the dark foliage (FIG. 3). However, except for the tendency not to change to bronze in the winter, color is not considered a distinguishing characteristic of the new variety. Like most redwoods, the new variety does not set a sealed winter bud. Male flowers (strobili) begin development, but most abort. Female flowers (strobili) begin development, but then typically convert to branch growth. See FIG. 4. The new variety appears to be sterile.

EASE OF ASEXUAL REPRODUCTION

Most cuttings root within 6 months and in high percentages (80+%) with standard procedures. Cutting donors may be repeatedly hedged to about 30–40 cm height for efficient cutting production. It does not appear that there will be any difficulties with routine large-scale vegetative reproduction. The rooted cuttings should be grown for about a year under good nursery conditions before transplanting. See FIG. 5. Container-grown plants that are larger than the yearling plant in FIG. 5 are suggested for many landscaping purposes.

We claim:

1. The new and distinct variety of redwood (*Sequoia sempervirens*), useful for Christmas tree and ornamental purposes, as herein described, characterized particularly by a dense columnar form, sometimes with upturning lower branches, slow growth, blue green winter color with buff or yellowish winter meristems, unusual cones, and ease of vegetative propagation.

* * * * *